United States Patent
Fujita (10) Patent No.: US 7,348,563 B2
(45) Date of Patent: Mar. 25, 2008

(54) TOMOGRAPHY IMAGING APPARATUS

(75) Inventor: Hiroshi Fujita, Saitama (JP)

(73) Assignee: Fujinon Corporation, Saitama (JP)

( * ) Notice: Subject to any disclaimer, the term of this patent is extended or adjusted under 35 U.S.C. 154(b) by 261 days.

(21) Appl. No.: 11/149,239

(22) Filed: Jun. 10, 2005

(65) Prior Publication Data

US 2005/0274894 A1 Dec. 15, 2005

(30) Foreign Application Priority Data

Jun. 14, 2004 (JP) .......................... P.2004-175401

(51) Int. Cl.
*G01T 1/166* (2006.01)
(52) U.S. Cl. ............................... 250/363.04
(58) Field of Classification Search ........... 250/363.04; 600/425; 356/479; 378/21
See application file for complete search history.

(56) References Cited

U.S. PATENT DOCUMENTS

| | | | |
|---|---|---|---|
| 7,095,505 B1* | 8/2006 | Beard et al. | 356/502 |
| 2002/0051515 A1* | 5/2002 | Saotome et al. | 378/95 |
| 2005/0036150 A1* | 2/2005 | Izatt et al. | 356/479 |
| 2005/0171438 A1* | 8/2005 | Chen et al. | 600/476 |

FOREIGN PATENT DOCUMENTS

JP 2001-272332 10/2001

OTHER PUBLICATIONS

Hauger et al., Interferometer for Optical Coherence Tomography, Jul. 1, 2003, Applied Optics, vol. 42, No. 19, pp. 3896-3902.*
Manabu Sato, et al., "Fundamentals of Optical Coherence Tomography," *Optics*, 2003, pp. 268-274, vol. 32, No. 4.

* cited by examiner

*Primary Examiner*—David Porta
*Assistant Examiner*—Djura Malevic
(74) *Attorney, Agent, or Firm*—Oliff & Berridge, PLC (57) ABSTRACT

A tomography imaging apparatus comprises: a light source that emits light having a low interferable performance; a light irradiation optical system constituted to split the light emitted from the light source into two, irradiate one of the split light to a subject and irradiate the other one of the split light to a reference mirror; a first guiding member that guides signal light to a first light emitting end, the signal light being from the subject based on light irradiation from the light irradiation optical system; a second light guiding member that guides reference light to a second light emitting end, the reference light being from the reference mirror based on the light irradiation; and a multipixel image taking element that provides an optical intensity distribution of interfered light by the signal light emitted from the first light emitting end and the reference light emitted from the second light emitting end.

21 Claims, 5 Drawing Sheets

TOMOGRAPHY IMAGING APPARATUS

RELATED APPLICATIONS

This application claims the priority of Japanese Patent Application No. 2004-175401, filed on Jun. 14, 2004, which is incorporated herein by reference.

BACKGROUND OF THE INVENTION

1. Field of the Invention

The present invention relates to a tomography imaging apparatus used when a tomographic image of a subject is provided in medical or industrial field by applying a method by Optical Coherence Tomography (hereinafter, referred to as OCT) constituted by combining a light source for outputting light having a short coherence length and an equal light pass length interferometer of a Michelson interferometer or the like, particularly relates to a tomography imaging apparatus which does not need a reference face scanning mechanism for providing image data in a depth direction of a subject.

2. Description of the Related Art

In recent years, in a field of taking an image of a subject for medical use or industrial use, particularly in a field of an electronic endoscope, there is known an apparatus of taking a tomographic image of a subject by using a method of OCT.

Since light is used as a detection probe, the tomography imaging apparatus by OCT does not pose a problem of exposing a subject to X-ray irradiation as in an X-ray image taking apparatus of a background art, and is extremely preferable particularly when the subject is the human body. Further, a large-sized apparatus such as CT, MRI or the like is not needed, a subject can simply be inspected and therefore, a burden in view of cost and a burden in view of physical strength of a subject can be alleviated, which is preferable also in this respect.

Further, since interfered wave information at respective positions in a depth direction of a subject is provided by utilizing low coherence performance of light having a wide band of a spectrum width, the tomography imaging apparatus using OCT can detect reflected light from inside of a subject by a spatial resolution of $\mu m$ order and can considerably promote a measurement resolution in comparison with an X-ray imaging apparatus of a background art.

A tomography imaging apparatus using OCT having such a number of excellent properties is disclosed in, for example, Optics vol. 32-4 (2003): by Manabu Sato, Naohiro Tanno or the like shown below.

Figure 5:
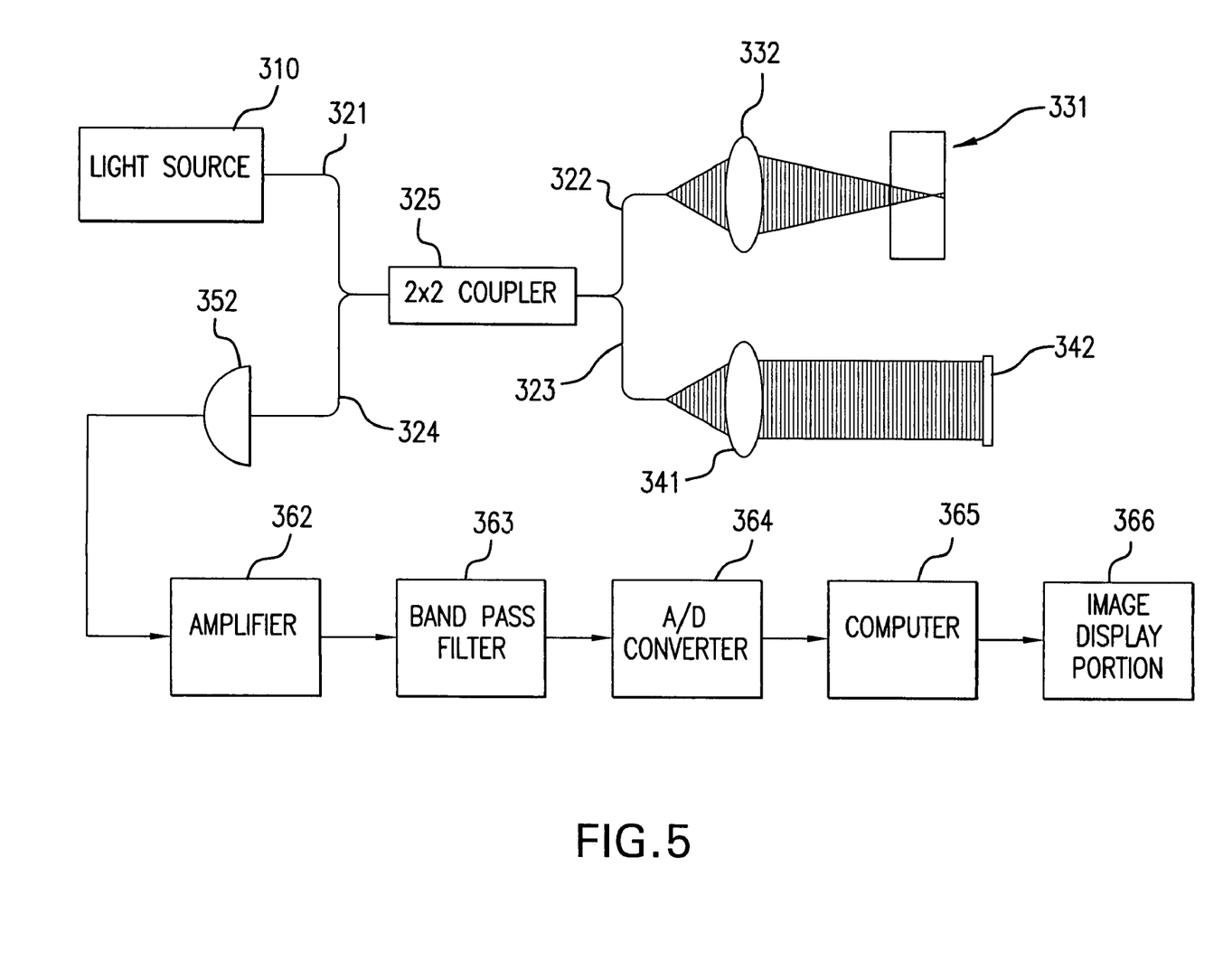
FIG. 5 is an outline view showing a tomography imaging apparatus according to a background art.

FIG. 5 shows an outline of a tomography imaging apparatus of a background art. That is, an output from a low interferable light source 310 is made to be incident on an optical fiber 321. A light flux progressing in the optical fiber 321 is separated into two light fluxes by a 2×2 coupler 325, one of the fluxes is guided to a side of a subject 331 by an optical fiber 322, and other thereof is guided to a side of a reference mirror 342 by an optical fiber 323.

An object converging lens 332 is provided at a post stage of a light emitting end of the optical fiber 322 and the light flux is converged to the subject 331 by the lens 332.

On the other hand, light emitted from a light emitting end of the optical fiber 323 is irradiated to the reference mirror 342 via a collimator lens 341, the reference mirror 342 is made to be movable in an optical axis direction, and the reference mirror 342 is moved to a position at which an optical path length from the light emitting end of the optical fiber 322 to an observing position in a depth direction of the subject 331 and an optical path length from the light emitting end of the optical fiber 323 to the reference mirror 342 are equal to each other. Thereby, there is constructed an interferometer of a so-to-speak Michelson type capable of interfering light even by low interferable light, and interfered wave information of respective positions in the depth direction of the subject 331 is provided.

Reflected light from the observing position of the subject 331 and reflected light from the reference mirror 342 respectively regress on irradiation paths thereof, combined by the 2×2 coupler 325 to interfere with each other, the interfered light reaches an optical detector 352 via an optical fiber 324 and the interfered wave information is detected by the optical detector 352. Thereafter, the interfered light information detected by the optical detector 352 is converted into an electric signal and is inputted to a computer 365 via an amplifier 362, a band pass filter 363, and an A/D converter 364 to subject to predetermined image processing.

Such an OCT technology is referred to as TDOCT (Time Domain OCT) in which a drive mechanism of repeatedly moving the reference mirror in the optical axis direction is needed and the apparatus is large-sized and complicated.

Hence, there has been developed a technology referred to also as SDOCT (Spectral Domain OCT) dispensing with a drive mechanism for moving a reference mirror. The SDOCT is arranged with, for example, a diffraction grating and a Fourier transformation optical system on a face at which the reflected light (signal light) from the subject and the reflected light (reference light) from the reference mirror are superposed, and by subjecting the provided interference wave information to Fourier transformation operation, a tomographic image of the subject can be provided without driving the reference mirror.

Such an SDOCT technology described in JP-A-2001-272332, shown below, is known.

Further, the technology described in JP-A-2001-272332 further adopts an angular dispersion imaging method capable of directly detecting an envelope of an interference signal.

However, according to the above-described technology described in JP-A-2001-272332, an interference signal representing an optical intensity distribution of interfered light provided by the optical detector is multiplied by a cosine function constituting a variable by a phase difference $\Delta 1$ of signal light and the reference light as a weight and therefore, an amplitude cannot accurately be detected when an angle $\theta$ of the function becomes $\pi/2$, $3\pi/2$ or the like.

Further, the optical members starting from the diffraction grating are arranged between light emitting faces and light detecting faces of the signal light and the reference light and an apparatus having a simpler constitution has been desired.

SUMMARY OF THE INVENTION

The invention has been carried out in view of the above-described situation and it is an object thereof to provide a tomography imaging apparatus dispensing with a drive mechanism for moving a reference mirror and capable of accurately detecting an amplitude of an interference signal while a constitution thereof is extremely simple.

A first tomography imaging apparatus of the invention comprises:

a light source for emitting light having a low interferable performance;

a light irradiation optical system constituted to split the light emitted from the light source into two, irradiate one of the split light to a subject and irradiate other thereof to a reference mirror;

a first guiding member for guiding signal light from the subject based on light irradiation from the light irradiation optical system to a light emitting end;

a second light guiding member for guiding reference light from the reference mirror based on the light irradiation to a light emitting end; and a multipixel image taking element for providing an optical intensity distribution of interfered light by the signal light emitted from the light emitting end of the first light guiding member and the reference light emitted from the light emitting end of the second light guiding member.

In this case, the emitting ends of the first light guiding member and the second light guiding member function as point light sources and arranged such that an optical positional relationship of the two emitting ends and the multipixel image taking element constitute a Young's interferometer.

Further, a second tomography imaging apparatus of the invention comprises:

a light source for emitting light having a low interferable performance;

a light irradiation optical system constituted to split light emitted from the light source into two, irradiate one of the split light to a subject and irradiate other thereof to a reference mirror;

a first light guiding member for splitting signal light from the subject based on light irradiation from the light irradiation optical system and guiding split first signal light and split second signal light respectively to light emitting ends different from each other such that the second light signal light produces a predetermined phase shift relative to the split first signal light;

a second light guiding member for splitting reference light from the reference mirror based on the light irradiation and guiding split first reference light and split second reference light to light emitting ends different from each other such that the split second reference light produces a predetermined phase shift relative to the split first reference light;

a first multipixel image taking element for providing an optical intensity distribution signal of interfered light by the first signal light emitted from the light emitting end of the first light guiding member and the first reference light emitted from the light emitting end of the second light guiding member;

a second multipixel image taking element for providing an optical intensity distribution signal of interfered light by the second signal light emitted from the light emitting end of the first light guiding member and the second reference light emitted from the light emitting end of the second light guiding member; and an optical intensity distribution difference constituting section that calculates a difference between the optical intensity distribution signal provided by the first multipixel image taking element and the optical intensity distribution signal provided by the second multipixel image taking element.

In this case, the respective emitting ends of the first light guiding member and the second light guiding member function as point light sources and arranged such that a positional relationship of the emitting end in correspondence with the first multipixel image taking element and the first multipixel image taking element and a positional relationship of the emitting end in correspondence with the second multipixel image taking element and the second multipixel image taking element respectively constitute Young's interferometers.

Further, the first light guiding member and the second light guiding member comprise, for example, optical fibers.

Further, it is preferable to constitute such that an object lens is inserted between the respective emitting ends of the first light conducting member and the second light conducting member and the multipixel image taking element and a position of the object lens is set such that a region of overlapping the signal light and the reference light corresponding to each other from the respective emitting ends is increased on the multipixel image taking element.

Further, it is preferable to further comprise light scanning section that scans light from the light source in a predetermine direction along a surface of the subject.

Further, it is preferable that the reference mirror is made to be movable in an optical axis direction of the reference mirror.

Further, it is preferable that the multipixel image taking element is made to be movable in an optical axis direction of the multipixel image taking element, and a sampling pitch in the depth direction of the subject is made to be variable.

Further, it is preferable to further comprise a tomography image information calculating section that calculates to analyze tomography image information of the subject based on an output signal from the multipixel image taking element and a scanning timing of the light scanning section, and a tomography image displaying section for displaying the tomography image information provided by the tomography image information calculating section.

DETAILED DESCRIPTION OF THE INVENTION

A tomography imaging apparatus according to an embodiment of the invention will be explained in reference to the drawings as follows.

Figure 1:
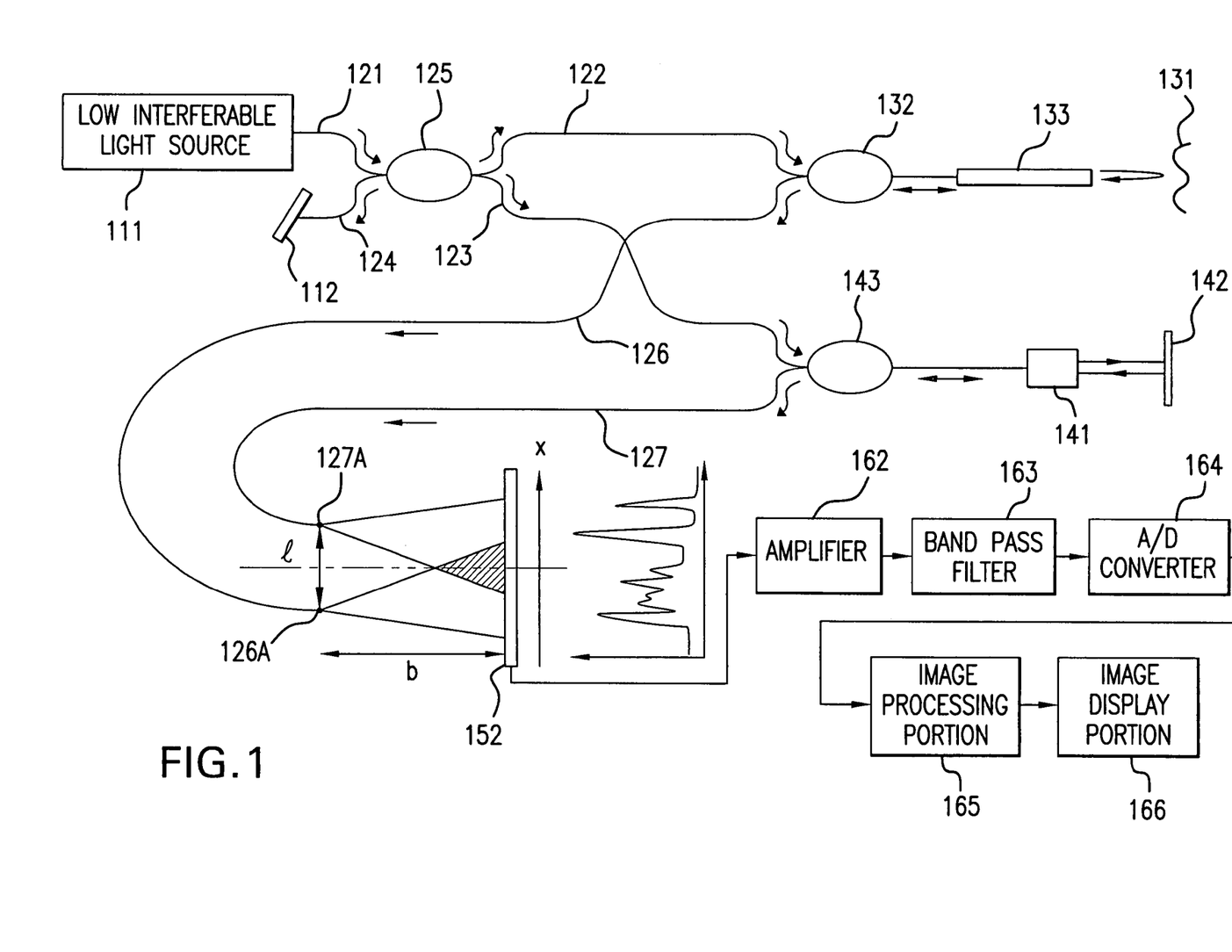
FIG. 1 is an outline view showing a tomography imaging apparatus according to a first embodiment of the invention.

FIG. 1 is an outline view showing a tomography imaging apparatus according to a first embodiment of the invention.

The tomography imaging apparatus according to the embodiment is applied to an endoscope for medical use and comprises a light source portion, an interferometer apparatus portion and a signal processing portion.

The light source portion comprises a low interferable light source 111. Further, the interferometer apparatus portion comprises a light irradiation optical system portion, guiding portions of signal light and reference light, and a Young's interferometer portion to constitute a Michelson interferometer apparatus of a so-to-speak unbalance type as a whole. The light irradiation optical system portion comprises four optical fibers 121, 122, 123, 124 and an optical coupler (2×2 coupler) 125, a first and a second optical circulator 132, 143, a light guiding member 133 arranged at a prestage of a subject 131, a collimator lens 141 and a reference mirror 142. Further, guiding portions of signal light and reference light comprise two optical fibers 126, 127. Further, the Young's interferometer portion is provided with emitting ends 126A, 127A of the two optical fibers 126, 127 respectives of which can be regarded as point light sources, and a multichannel detector 152 (multiple image taking element) for providing an interference signal by taking an image of interference fringes carrying subject information.

Further, the signal processing portion is constituted by including an amplifier 162, a band pass filter 163, an A/D converter 164, an image processing portion 165, and an image display portion 166.

Operation of the above-described embodiment apparatus will be explained as follows.

The low interferable light source 111 is a light source for emitting light having a wide spectrum width (wide wavelength band) in a near infrared region (also referred to as low interferable light as follows) and comprises, for example, SLD (Super-luminescent diode) or ASE (Amplified Spontaneous Emission) light source or the like. Light emitted from the low interferable light source 111 is converged to an incident end face of the optical fiber 121 by a converging lens, not illustrated, and is transmitted to the optical coupler (2×2 coupler) 125 by the optical fiber 121.

The transmitted low interferable light is split into two by the optical coupler 125, one of split light is transmitted by the optical fiber 122 and other thereof is transmitted by the optical fiber 123. Further, the optical coupler (2×2 coupler) 125 is connected with an optical detector 112 for detecting an optical intensity of the low interferable light source 111 via the optical fiber 124.

Low interferable light transmitted by the optical fiber 122 is converged to irradiate the subject 131 (human body) via the first circulator 132 and the light guiding member 133.

Low interferable light irradiated to the subject 131 is reflected from respective positions in a depth direction of the subject 131 to constitute signal light, regresses in an irradiation path thereof and is guided to the Young's interferometer portion by the first optical fiber 126.

On the other hand, low interferable light transmitted by the optical fiber 123 is irradiated to the reference mirror 142 via the second optical circulator 143 and the collimator 141.

Low interferable light (reference light) reflected from the reference mirror 142 regresses in an irradiation path thereof and is irradiated to the Young's interferometer portion by the optical fiber 127.

The signal light and the reference light guided to the Young's interferometer portion interfere with each other at the Young's interferometer portion and image information in the depth direction of the subject is detected by the mutlichannel detector 152 as a change in an optical intensity (optical intensity distribution).

Thereafter, the optical intensity distribution detected by the mutlichannel detector 152 is converted into an electric signal and is inputted to the image processing portion 165 via the amplifier 162, the band pass filter 163, the A/D converter 164 to generate image information in the depth direction of the subject 131 and the generated image information in the depth direction is displayed at the image display portion 166.

Further, at the image processing portion 165, a one-dimensional optical intensity signal outputted from the multichannel detector 152 and carrying information in the depth direction of the subject 131 is subjected to an envelope processing. That is, since the optical intensity signal emerges in a mode of an alternating current signal, the optical intensity signal is converted into a signal having only a plus component by folding back a minus component and thereafter, the envelope is extracted to provide the continuous optical intensity signal.

Thereafter, the continuous optical intensity signal is outputted to the image display portion 166 and a tomography image at the subject 131 is displayed.

Further, generally, the optical intensity distribution in the depth direction is provided at respective scanning points by an optical scanning section that scans illuminating light in a predetermined direction along a surface of the subject 131 and at the image processing portion 165, an image signal processing for connecting the light intensity distributions in the depth direction of the respective points is executed to generate a two-dimensional tomographic image signal.

The Young's interferometer portion constituting a principal point of the invention will be explained in details as follows.

The signal light and the reference light guided to the Young's interferometer portion as described above are emitted from the emitting end 126A of the first optical fiber 126 and the emitting end 127A of the second optical fiber 127. Here, fiber core diameters of the emitting ends 126A, 127A of the respective optical fibers 126, 127 are normally 9 through 10 μm and therefore, the respective emitting ends may be regarded as point light sources. Here, when a distance between centers of the respective emitting ends 126A, 127A is set to 1 and a distance from a line segment connecting the respective emitting ends 126A, 127A to the mutlichannel detector 152 arranged in parallel with the line segment (the direction is defined as x direction) is set to b, on the multichannel detector 152, in accordance with a position x in X direction, a light path difference as shown by Equation (1), shown below, is produced between a light path length S1 of reference light from the emitting end 127A and a light path length S2 of signal light from the emitting end 126A.

$$s_1 - s_2 = -\frac{bx}{l} \qquad (1)$$

Meanwhile, according to the generally known Young's interferometer, light from the light source is dealt with as light having a short wavelength and a sufficiently long coherence length and therefore, when a wave face of the same phase from the same light source is split into two, an intensity distribution f(x) at an evaluation face (image taking element face) becomes a sine wave as shown by Equation (2), shown below. Here, notation λ designates a wavelength used.

$$f(x) \propto 1 + \cos\left(-k \cdot \frac{bx}{l}\right) \qquad (2)$$

where k=2π/λ

In contrast thereto, when the light source is the low interferable light source used in OCT, assuming that phases of light waves at the emitting ends 126A, 127A of the respective optical fibers 126, 127 coincide with each other, an intensity distribution g(x) at the evaluation face (image taking element face) is represented by Equation (3), shown below.

$$g(x) = \int S(\lambda)\left\{1 + \cos\left(-k \cdot \frac{bx}{l}\right)\right\}d\lambda \qquad (3)$$

where $k=2\pi/\lambda$

That is, on the multichannel detector 152, interference fringes are produced only at a small region centering on an optical path difference of 0.

Further, when signal light is provided with a time delay amount relative to reference light, as is apparent from development of Equation (3), mentioned above, a position of producing interference fringes emerges at a position shifted from the position of the optical path difference of 0 by a predetermined amount in X direction in accordance with a time delay amount (depth amount). Thereby, image information in accordance with the depth of the subject 131 can be developed on the one-dimensional multichannel detector 152.

Further, in the above-described embodiment, the reference mirror 142 may be constituted to be movable in the optical axis direction, thereby, a detection range in the depth direction of the subject 131 can be changed.

Further, in the above-described embodiment, the multichannel detector 152 may be constituted to be movable in the optical axis direction, thereby, a sampling pitch in detection can be made to be variable.

Further, a front end of the light guiding member 133 is provided with an object converging lens for converging illuminating light to irradiate the subject 131 and therefore, when at least a portion of the lens is constituted to be movable to be able to focus the observing position, out of focus of the subject image at the observing position can be prevented.

Figure 2:
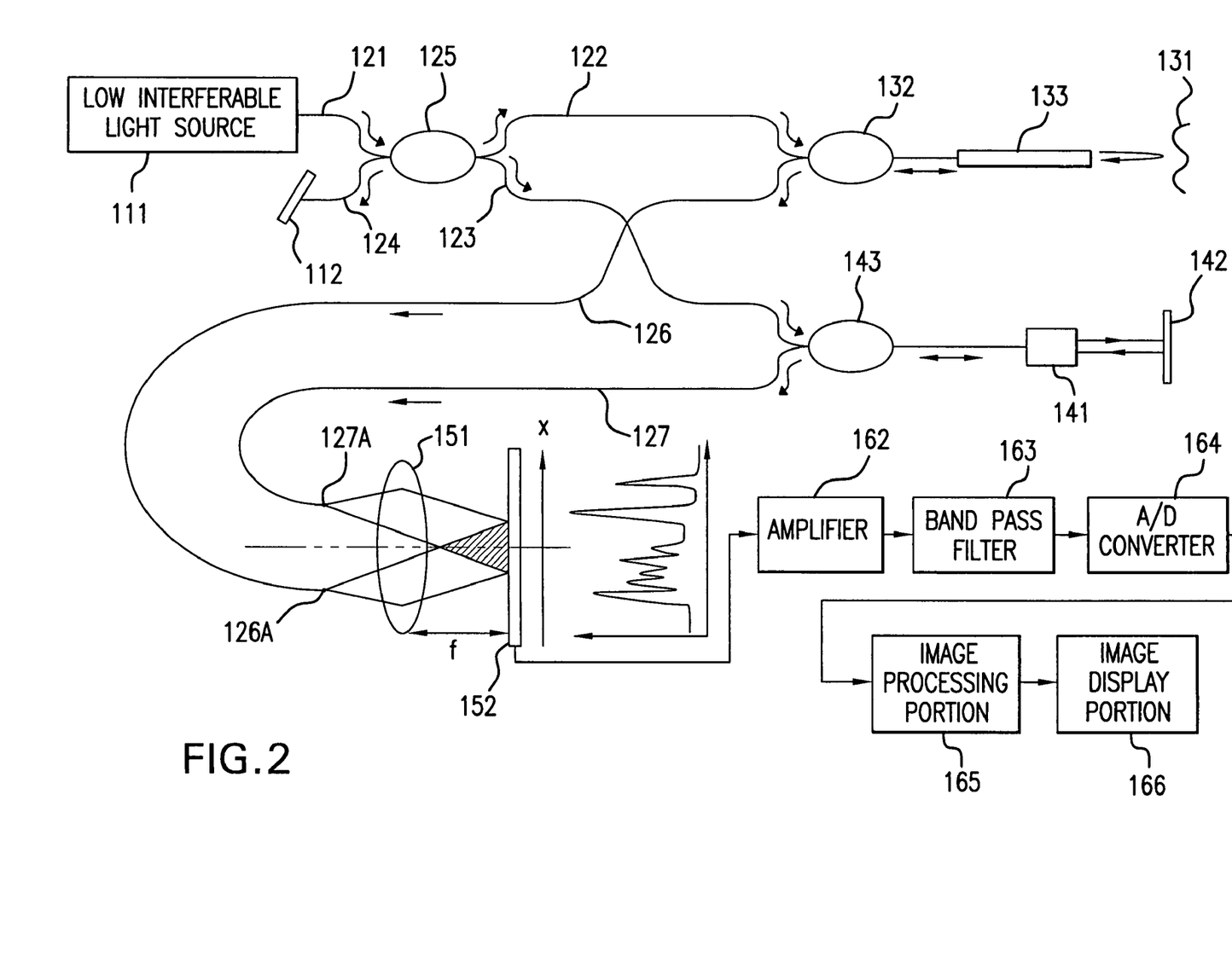
FIG. 2 is an outline view showing a tomography imaging apparatus according to a second embodiment of the invention.

Further, FIG. 2 is an outline constitution view showing a tomography imaging apparatus according to a second embodiment of the invention. The embodiment is constructed by a constitution the same as that of the first embodiment except the Young's interferometer portion and therefore, members in FIG. 2 the same as those of FIG. 1 are attached the same notations and a detailed explanation thereof will be omitted.

According to the embodiment, an object lens 151 is arranged at the Young's interferometer portion.

Further, the emitting ends 126A, 127A of the respective optical fibers 126, 127 are arranged at positions symmetric with each other relative to an optical axis of the object lens 151 and states of expanding and converging signal light and reference light emitted from the respective emitting ends 126A, 127A are adjusted by the object lens 151.

Thereby, positions of irradiating signal light and reference light on the multichannel detector 152 can be constituted by optimal positions in accordance with a specification of a size of the multichannel detector 152 and a resolution (pixel number) thereof and a light amount of a region of the multichannel detector 152 overlapping signal light and reference light (interference region: hatched region in the drawing) can considerably be increased in comparison with the first embodiment.

Further, particularly when an element face of the multichannel detector 152 is arranged at a position of a focal face of the object lens 151 (f in FIG. 2 is, for example, 50 mm), the interference region of signal light and reference light is constituted by a shape symmetric with respect to the optical axis of the object lens 151 and the position of the multichannel detector 152 is facilitated to set.

Figure 3:
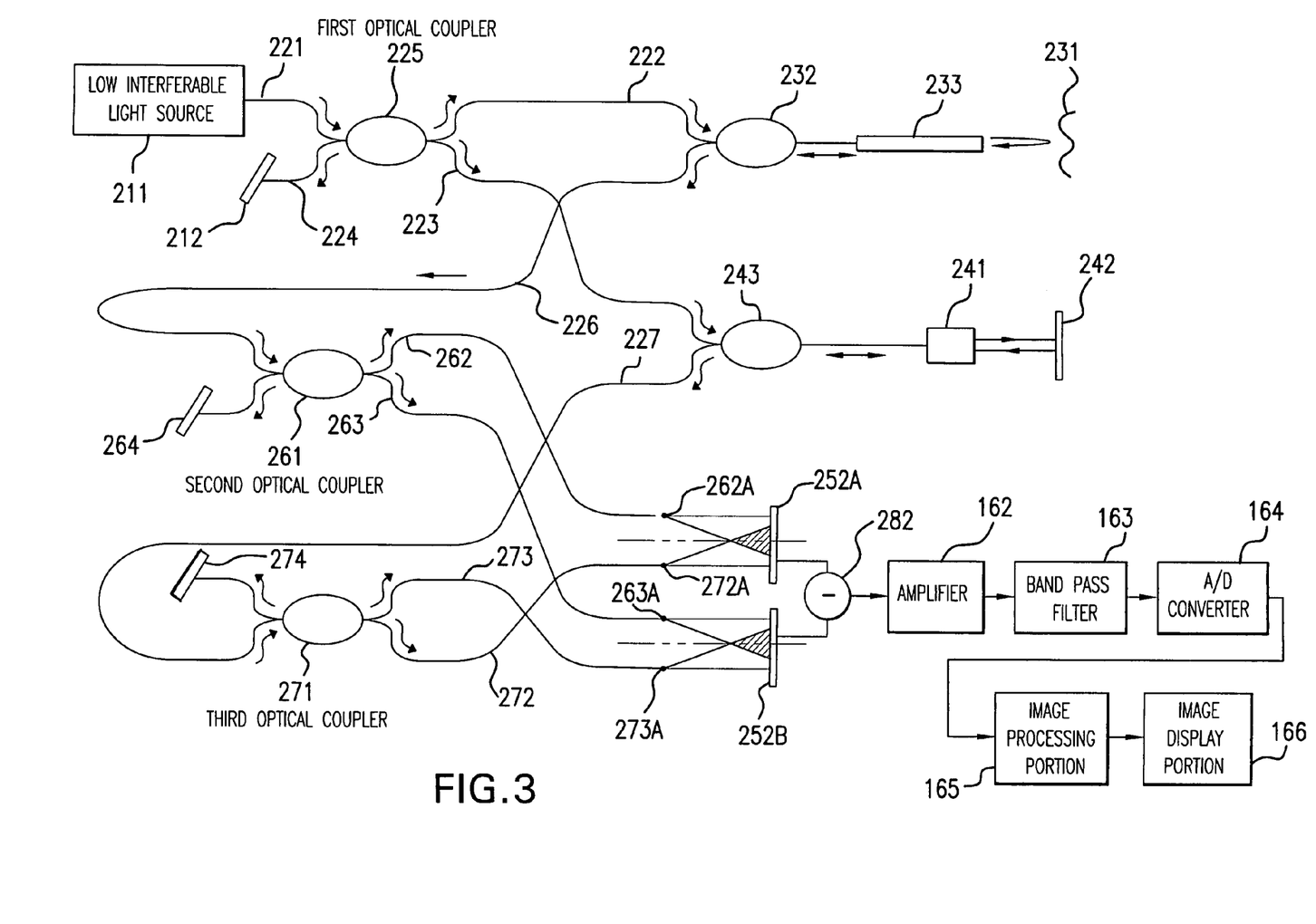
FIG. 3 is an outline view showing a tomography imaging apparatus according to a third embodiment of the invention.

Further, FIG. 3 is an outline constitution view showing a tomography imaging apparatus according to a third embodiment of the invention. The embodiment is provided with a number of constitutions in correspondence with those of the first embodiment and therefore, members of FIG. 3 in correspondence with those of FIG. 1 are attached with notations adding 100 to the notations of FIG. 1 (however, the same notations are attached to 162 through 166) and a detailed explanation thereof will be omitted.

A point of the embodiment which differs from the above-described two embodiments resides in that a bias components including also a fluctuation of the light source are canceled by introducing a method of balance detection.

That is, as shown by FIG. 3, signal light guided by a first optical fiber 226 is split into first signal light and second signal light subjected to phase modulation of $\pm\pi/2$ relative to the first signal light by a second optical coupler (3 dB coupler) 261, the former is guided to a first emitting end 262A by an optical fiber 262, and the latter is guided to a second emitting end 263A by an optical fiber 263. On the other hand, reference light guided by a second optical fiber 227 is split into first reference light and second reference light subjected to phase modulation of $\pm\pi/2$ relative to the first reference light by a third optical coupler (3 dB coupler) 271, the former is guided to a third emitting end 272A by an optical fiber 272 and the latter is guided to a fourth emitting end 273A by an optical fiber 273. Further, the respective optical couplers 261, 271 are connected with isolators 264, 274.

The first emitting end 262A and the third emitting end 272A and a first multichannel detector 252A (first multiple image taking element) constitute a first Young's interferometer functioning similar to the Young's interferometer of the first embodiment. On the other hand, the second emitting end 263A and the fourth emitting end 273A and a second multichannel detector 252B (second multiple image taking element) constitute a second Young's interferometer functioning similar to the Young's interferometer of the first embodiment.

Respective pieces of interfered wave information detected by the first multichannel detector 252A and the second multichannel detector 252B are converted into electric signals and thereafter made to constitute a difference by each other at a difference operator 282 and the difference is inputted to the image processing portion 165 via the amplifier 162, the band pass filter 163, the A/D converter 164 to generate a tomography image of a subject 231 similar to the above-described two embodiments. The generated tomography image is displayed by the image display portion 166.

Figure 4:
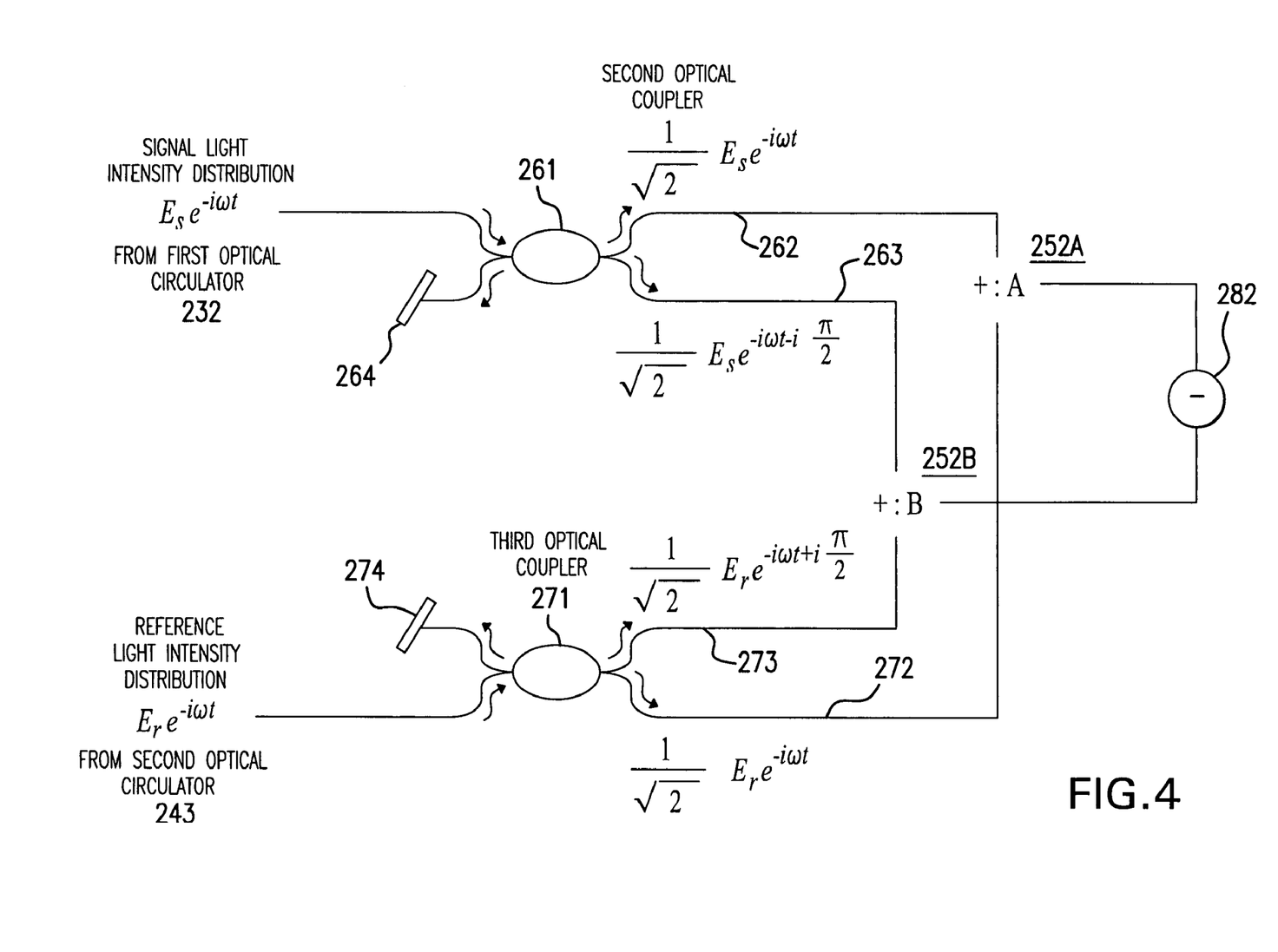
FIG. 4 is a schematic view for explaining operation of a portion of FIG. 3.

According to the embodiment, by introducing the method of balance detection, a bias component (including also a fluctuation of light source) in an interference wave can be removed and only an interference wave component can be extracted. That is, a characteristic portion of the embodiment is expressed as shown by FIG. 4 and signal light and reference light are divided into pieces of signal light and reference light having illustrated intensity distributions by the respective optical couplers 261, 271.

Further, an intensity distribution of an interference signal A provided at the first multichannel detector 252A and an intensity distribution of an interference signal B provided at the second multichannel detector 252B are expressed by Equation (4) and Equation (5), shown below. Further, in the following equations, notation Es designates an optical intensity of signal light, notation Er designates an optical intensity of reference light, notation ω designates a frequency of a light wave and notation * designates an imaginary number.

$$A = \left| \frac{1}{\sqrt{2}} E_r e^{-iwt} + \frac{1}{\sqrt{2}} E_s e^{-iwt} \right|^2 = \frac{1}{2}|E_r|^2 + \frac{1}{2}|E_s|^2 + \frac{1}{2}(E_r E_s^* + E_r^* E_s) \quad (4)$$

$$B = \left| \frac{1}{\sqrt{2}} E_r e^{-iwt - i\frac{\pi}{2}} + \frac{1}{\sqrt{2}} E_s e^{-iwt + i\frac{\pi}{2}} \right|^2 = \quad (5)$$

$$\left( \frac{1}{\sqrt{2}} E_r e^{-iwt - i\frac{\pi}{2}} + \frac{1}{\sqrt{2}} E_s e^{-iwt + i\frac{\pi}{2}} \right)$$

$$\left( \frac{1}{\sqrt{2}} E_r^* e^{iwt + i\frac{\pi}{2}} + \frac{1}{\sqrt{2}} E_s^* e^{iwt - i\frac{\pi}{2}} \right) =$$

$$\frac{1}{2}|E_r|^2 + \frac{1}{2}|E_s|^2 - \frac{1}{2}(E_r E_s^* + E_r^* E_s)$$

Therefore, an interference signal outputted from the difference operator 282 is expressed by Equation (6), shown below.

$$A - B = (E_r E_s^* + E_r^* E_s) \quad (6)$$

It is apparent from Equation (6), mentioned above, that in the interference signal, the bias components are canceled by each other and only the interference signal component is multiplied by two.

Further, also according to the above-described third embodiment, similar to the first and the second embodiments, an optical scanning section that scans illuminating light in a predetermined direction along the surface of the subject 231 is provided, the optical intensity distribution in the depth direction of respective points provided in accordance with the scanning is provided and at the image processing portion 165, the image signal processing of connecting the optical intensity distribution in the depth direction of the respective points is executed to generate the two-dimensional tomographic image signal.

Further, by arranging lenses similar to the object lens 151 constituting the characteristic of the above-described second embodiment at the respective Young's interferometers of the third embodiment, also the effect of the above-described second embodiment can be achieved.

Further, also according to the third embodiment, similar to the above-described first and second embodiments, the detection range in the depth direction of a subject 231 can be changed by constituting a reference mirror 242 to be movable in the optical axis direction and the sampling pitch in detection can be made to be variable by constituting the respective multichannel detectors 252A, 252B movably in the optical axis directions.

Further, similar to the above-described first and second embodiments, by making the object converging lens provided at a front end of a light guiding member 233 for converging to irradiate illuminating light to the subject 231 movable in the optical axis direction, out of focus of the subject image at the observing position may be prevented.

Further, according to the tomography imaging apparatus of the invention, the other mode can be changed, for example, as the low interferable light source, in place of the above-described light source, a well-known low interferable light source of a normal diode, a high pressure mercury lamp or the like can be used.

Further, although the one-dimensional multichannel detector is conceived in the above-described respective embodiments, the multipixel image taking element of the tomography imaging apparatus of the invention is not limited thereto but, for example, may be a face sensor for detecting light two-dimensionally. A tomography imaging apparatus using a face sensor is described in "Nonscanning OCT measurement using angular dispersion imaging method" (Umezu, Akiba, Chin, Tanno), proceeding of Optics Japan 2003 pp. 102-103 or the like.

Further, although in the above-described embodiment, the Michelson type of the equal optical path length type interferometer is used, in place thereof, other equal optical path length type interferometer of a Mach-Zender type or the like may be used.

Further, the subject is not limited to the human body but can be constituted by other various structures in which light invades inside thereof and reflected light is provided from respective positions of the inside.

According to the first tomography imaging apparatus of the invention, the tomography image information in the depth direction of the subject is acquired by making the signal light and the interference light interfere with each other by the Young's interferometer (common path interferometer) regarding the emitting ends of the light guiding members for guiding the signal light from the subject and the reference light from the reference mirror as the point light sources and detecting the interference signal by the multipixel image taking element.

Generally, the Young's interferometer (or common path interferometer) is known to make two pieces of light from the same light source in which a time delay is not produced interfere with each other and in the case of a light source having a sufficiently long coherence length, the interference signal becomes a sine wave.

Further, the inventors have found that an extremely simple tomography imaging apparatus can be constituted when a concept of the Young's interferometer (or common path interferometer) is applied to OCT constituting an indispensable element by the low interferable light source and producing a time delay between two pieces of light to be interfered with each other to reach to carry out the invention.

That is, since low interferable light is used in OCT, when the concept of the Young's interferometer (or common path interferometer) is introduced, interference fringes can be generated in an extremely narrow range centering on a position of a face of the image taking element at which a light path difference of two pieces of light becomes null. Therefore, since the signal light is provided with a time delay amount in accordance with the depth position of the subject relative to the reference light, a signal subjecting image information in correspondence with the depth position to convolution integration by interference wave information of the low interferable light source path per se is provided from the image taking element. Subject tomography image information similar to that of TDOCT of the background art can be provided by subjecting the signal to a filtering processing and a signal processing of a log amplifier or the like and shaping the signal.

Therefore, a mechanism of moving and scanning the reference mirror in the optical axis direction which has been indispensable in TDOCT of the background art, is not needed, further, an optical dispersion element of a diffraction grating or the like which has been used in SDOCT of the background art is not needed and the OCT apparatus which is fast in speed and simple and capable of accurately detecting the amplitude of the interference signal can be provided.

Further, the second tomography imaging apparatus of the invention basically achieves operation and effect similar to those of the above-described first tomography imaging apparatus and in addition thereto, by introducing a method of balance detection, an effect of capable of canceling a bias component including a fluctuation of a light source and theoretically doubling only an interference signal component can be achieved.

The entire disclosure of each and every foreign patent application from which the benefit of foreign priority has been claimed in the present application is incorporated herein by reference, as if fully set forth.

What is claimed is:

1. A tomography imaging apparatus comprising:
    a light source that emits light having a low interferable performance;
    a light irradiation optical system constituted to split the light emitted from the light source into two, irradiate one of the split light to a subject and irradiate the other one of the split light a reference mirror;
    a first light guiding member that splits signal light from the subject based on light irradiation from the light irradiation optical system so as to generate first signal light and second signal light and that guides the first signal light and the second signal light to a first light emitting end and a second light emitting end respectively such that the second light signal light produces a phase shift relative to the first signal light;
    a second light guiding member that splits reference light from the reference mirror based on the light irradiation so as to generate first reference light and second reference light and that guides the first reference light and the second reference light to a third light emitting end and a fourth light emitting end respectively such that the second reference light produces a phase shift relative to the split first reference light;
    a first multipixel image taking element that provides a first optical intensity distribution signal of interfered light by the first signal light emitted from the first light emitting end and the first reference light emitted from the third light emitting end;
    a second multipixel image taking element that provides a second optical intensity distribution signal of interfered light by the second signal light emitted from the second light emitting end and the second reference light emitted from the fourth light emitting end; and
    an optical intensity distribution difference constituting section that calculates a difference between the first optical intensity distribution signal and the second optical intensity distribution signal.

2. The tomography imaging apparatus according to claim 1,
    wherein each of the first, second, third and fourth light emitting ends functions as a point light source, and the first, second, third and fourth light emitting ends are arranged such that an optical positional relationship of the first and third light emitting ends and the first multipixel image taking element constitute a Young's interferometer and an optical positional relationship of the second and fourth light emitting ends and the second multipixel image taking element constitutes a Young's interferometer.

3. The tomography imaging apparatus according to claim 1,
    wherein each of the first light guiding member and the second light guiding member comprises optical fiber.

4. The tomography imaging apparatus according to claim 1,
    wherein a first object lens is inserted between the first and third emitting ends of the first and second light conducting members and the first multipixel image taking element, and second object lens is inserted between the second and fourth emitting ends of the first and second light conducting members and the second multipixel image taking element, and
    wherein a position of the first object lens is set such that a region of overlapping the first signal light from the first light emitting end and the first reference light from the third light emitting end is increased on the first multipixel image taking element, and a position of the second object lens is set such that a region of overlapping the second signal light from the second light emitting end and the second reference light from the fourth light emitting end is increased on the second multipixel image taking element.

5. The tomography imaging apparatus according to claim 1, further comprising:
    a light scanning section that scans light from the light source in a direction along a surface of the subject.

6. The tomography imaging apparatus according to claim 1,
    wherein the reference mirror is movable in an optical axis direction of the reference mirror.

7. The tomography imaging apparatus according to claim 1, wherein the first multipixel image taking element is movable in an optical axis direction of the first multipixel image taking element, and the second multipixel image taking element is movable in an optical axis direction of the second multipixel image taking element.

8. The tomography imaging apparatus according to claim 5, further comprising:
    a tomography image information calculating section that calculates to analyze tomography image information of the subject based on an output signal from the first and second multipixel image taking elements and a scanning timing of the light scanning section; and
    a tomography image displaying section that displays the tomography image information provided by the tomography image information calculating section.

9. The tomography imaging apparatus comprising:
    a light source that emits light having a low interferable performance;
    a light irradiation optical system constituted to split the light emitted from the light source into two, irradiate one of the split light to a subject and irradiate the other one of the split light to a reference mirror;
    a first guiding member that guides signal light to a first light emitting end, the signal light being from the subject based on light irradiation from the light irradiation optical system;
    a second light guiding member that guides reference light to a second light emitting end, the reference light being from the reference mirror based on the light irradiation;
    a multipixel image taking element that provides an optical intensity distribution of interfered light by the signal light emitted from the first light emitting end and the reference light emitted from the second light emitting end; and
    wherein the multipixel image taking element is movable in an optical axis direction of the multipixel image taking element.

10. The tomography imaging apparatus according to claim 9, wherein each of the first and second light emitting ends functions as a point light source, and the first and second light emitting ends are arranged such that an optical positional relationship of the first and second light emitting ends and the multipixel image taking element constitutes a Young's interferometer.

11. The tomography imaging apparatus according to claim 9, wherein each of the first light guiding member and the second light guiding member comprises optical fiber.

12. The tomography imaging apparatus according to claim 9, further comprising:
a light scanning section that scans light from the light source in a direction along a surface of the subject.

13. The tomography imaging apparatus comprising:
a light source that emits light having a low interferable performance;
a light irradiation optical system constituted to split the light emitted from the light source into two, irradiate one of the split light to a subject and irradiate the other one of the split light to a reference mirror;
a first guiding member that guides signal light to a first light emitting end, the signal light being from the subject based on light irradiation from the light irradiation optical system;
a second light guiding member that guides reference light to a second light emitting end, the reference light being from the reference mirror based on the light irradiation;
a multipixel image taking element that provides an optical intensity distribution of interfered light by the signal light emitted from the first light emitting end and the reference light emitted from the second light emitting end; and
wherein an object lens is inserted between the first and second emitting ends of the first and second light conducting members and the multipixel image taking element, and a position of the object lens is set such that a region of overlapping the signal light from the first light emitting end and the reference light from the second light emitting end is increased on the multipixel image taking element.

14. The tomography imaging apparatus according to claim 13, wherein each of the first and second light emitting ends functions as a point light source, and the first and second light emitting ends are arranged such that an optical positional relationship of the first and second light emitting ends and the multipixel image taking element constitutes a Young's interferometer.

15. The tomography imaging apparatus according to claim 13,
wherein each of the first light guiding member and the second light guiding member comprises optical fiber.

16. The tomography imaging apparatus according to claim 13, further comprising:
a light scanning section that scans light from the light source in a direction along a surface of the subject.

17. The tomography imaging apparatus according to claim 16, further comprising:
a tomography image information calculating section that calculates to analyze tomography image information of the subject based on an output signal from the multipixel image taking element and a scanning timing of the light scanning section; and
a tomography image displaying section that displays the tomography image information provided by the tomography image information calculating section.

18. The tomography imaging apparatus comprising:
a light source that emits light having a low interferable performance;
a light irradiation optical system constituted to split the light emitted from the light source into two, irradiate one of the split light to a subject and irradiate the other one of the split light to a reference mirror;
a first guiding member that guides signal light to a first light emitting end, the signal light being from the subject based on light irradiation from the light irradiation optical system;
a second light guiding member that guides reference light to a second light emitting end, the reference light being from the reference mirror based on the light irradiation;
a multipixel image taking element that provides an optical intensity distribution of interfered light by the signal light emitted from the first light emitting end and the reference light emitted from the second light emitting end; and
wherein the reference mirror is movable in an optical axis direction of the reference mirror.

19. The tomography imaging apparatus according to claim 18, wherein each of the first and second light emitting ends functions as a point light source, and the first and second light emitting ends are arranged such that an optical positional relationship of the first and second light emitting ends and the multipixel image taking element constitutes a Young's interferometer.

20. The tomography imaging apparatus according to claim 18, wherein each of the first light guiding member and the second light guiding member comprises optical fiber.

21. The tomography imaging apparatus according to claim 18, further comprising:
a light scanning section that scans light from the light source in a direction along a surface of the subject.

* * * * *